(12) United States Patent
Allen et al.

(10) Patent No.: US 7,060,064 B2
(45) Date of Patent: Jun. 13, 2006

(54) ELECTROSURGICAL ELECTRODE SHROUD

(75) Inventors: Charles Allen, Broomfield, CO (US); Joe Don Sartor, Longmont, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 11/165,891

(22) Filed: Jun. 24, 2005

(65) Prior Publication Data

US 2005/0273098 A1    Dec. 8, 2005

Related U.S. Application Data

(63) Continuation of application No. 10/358,450, filed on Feb. 4, 2003, now Pat. No. 6,986,768.

(51) Int. Cl.
*A61B 18/14* (2006.01)

(52) U.S. Cl. ............................ 606/41; 606/45; 606/49

(58) Field of Classification Search .................. 606/41, 606/42, 45, 49
See application file for complete search history.

(56) References Cited

U.S. PATENT DOCUMENTS

| | | | |
|---|---|---|---|
| 3,460,539 A | 8/1969 | Anhalt, Sr. |
| 3,825,004 A | 7/1974 | Durden, III |
| 3,828,780 A | 8/1974 | Morrison, Jr. |
| 3,902,494 A | 9/1975 | Haberlen et al. |
| 3,906,955 A | 9/1975 | Roberts |
| 3,967,084 A | 6/1976 | Pounds |
| 3,974,833 A | 8/1976 | Durden, III |
| 4,032,738 A | 6/1977 | Esty et al. |
| 4,034,762 A | 7/1977 | Cosens et al. |
| 4,232,676 A | 11/1980 | Herczog |
| 4,314,559 A | 2/1982 | Allen |
| 4,427,006 A | 1/1984 | Nottke |
| 4,459,443 A | 7/1984 | Lewandowski |
| 4,463,234 A | 7/1984 | Bennewitz |
| 4,492,231 A | 1/1985 | Auth |
| 4,562,838 A | 1/1986 | Walker |
| 4,625,723 A | 12/1986 | Altnether et al. |
| 4,640,279 A | 2/1987 | Beard |
| 4,642,128 A | 2/1987 | Solorzano |
| 4,683,884 A | 8/1987 | Hatfield et al. |
| 4,701,193 A | 10/1987 | Robertson et al. |
| 4,719,914 A | 1/1988 | Johnson et al. |
| 4,735,603 A | 4/1988 | Goodson et al. |
| 4,785,807 A | 11/1988 | Blanch |
| 4,827,911 A | 5/1989 | Broadwin et al. |
| 4,846,790 A | 7/1989 | Hornlein et al. |
| 4,850,353 A | 7/1989 | Stasz et al. |
| 4,862,890 A | 9/1989 | Stasz et al. |
| 4,869,715 A | 9/1989 | Sherburne |
| 4,886,060 A | 12/1989 | Wiksell |

(Continued)

FOREIGN PATENT DOCUMENTS

EP    1009302    6/2000

(Continued)

*Primary Examiner*—Lee S. Cohen

(57) ABSTRACT

An electrosurgical electrode shroud including a hollow substantially cylindrical member having a first end portion and a second end portion; the first end portion defining an opening which is configured and dimensioned to receive an electrosurgical electrode assembly therein; the second end portion defining an opening which is configured and dimensioned to receive an electrode mounting portion of an electrosurgical instrument, wherein at least the second end portion is formed of a substantially translucent material. The electrosurgical electrode shroud may further include visual or tactile indicator on the second end portion for indicating a depth of penetration of the electrosurgical instrument within the second end portion when viewed by the surgeon through the translucent material.

16 Claims, 4 Drawing Sheets

U.S. PATENT DOCUMENTS

| | | | |
|---|---|---|---|
| 4,901,719 A | 2/1990 | Trenconsky et al. |
| 4,909,249 A | 3/1990 | Akkas et al. |
| 4,911,159 A | 3/1990 | Johnson et al. |
| 4,916,275 A | 4/1990 | Almond |
| 4,921,476 A | 5/1990 | Wuchinich |
| 4,931,047 A | 6/1990 | Broadwin et al. |
| 4,986,839 A | 1/1991 | Wertz et al. |
| 4,988,334 A | 1/1991 | Hornlein et al. |
| 5,026,368 A | 6/1991 | Adair |
| 5,055,100 A | 10/1991 | Olsen |
| 5,071,418 A | 12/1991 | Rosenbaum |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,133,714 A | 7/1992 | Beane |
| 5,147,292 A | 9/1992 | Kullas et al. |
| 5,160,334 A | 11/1992 | Billings et al. |
| 5,162,044 A | 11/1992 | Gahn et al. |
| 5,178,605 A | 1/1993 | Imonti |
| 5,190,517 A | 3/1993 | Zieve et al. |
| 5,192,267 A | 3/1993 | Shapira et al. |
| 5,195,959 A | 3/1993 | Smith |
| 5,197,962 A | 3/1993 | Sansom et al. |
| 5,199,944 A | 4/1993 | Cosmescu |
| 5,217,457 A | 6/1993 | Delauherga et al. |
| 5,224,944 A | 7/1993 | Elliott |
| 5,226,904 A | 7/1993 | Gentelia et al. |
| 5,233,515 A | 8/1993 | Cosman |
| 5,234,428 A * | 8/1993 | Kaufman ................ 606/45 |
| 5,242,442 A | 9/1993 | Hirschfeld |
| 5,244,462 A | 9/1993 | Delahuerga et al. |
| 5,254,082 A | 10/1993 | Takase |
| 5,256,138 A | 10/1993 | Burek et al. |
| 5,269,781 A | 12/1993 | Hewell, III |
| 5,306,238 A | 4/1994 | Fleenor |
| 5,312,329 A | 5/1994 | Beaty et al. |
| 5,318,516 A | 6/1994 | Cosmescu |
| 5,318,565 A | 6/1994 | Kuriloff et al. |
| 5,334,183 A | 8/1994 | Wuchinich |
| RE34,780 E * | 11/1994 | Trenconsky et al. .......... 606/49 |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,484,398 A | 1/1996 | Stoddard |
| 5,486,162 A | 1/1996 | Brumbach |
| 5,498,654 A | 3/1996 | Shimasaki et al. |
| 5,531,722 A | 7/1996 | Van Hale |
| 5,549,604 A | 8/1996 | Sutcu et al. |
| 5,601,224 A | 2/1997 | Bishop et al. |
| 5,634,912 A | 6/1997 | Injev |
| 5,643,256 A | 7/1997 | Urueta |
| 5,669,907 A | 9/1997 | Platt, Jr. et al. |
| 5,693,050 A | 12/1997 | Speiser |
| 5,693,052 A | 12/1997 | Weaver |
| 5,697,926 A | 12/1997 | Weaver |
| 5,702,360 A | 12/1997 | Dieras et al. |
| 5,702,387 A | 12/1997 | Arts et al. |
| 5,713,895 A | 2/1998 | Lontine et al. |
| 5,720,745 A | 2/1998 | Farin et al. |
| 5,765,418 A | 6/1998 | Rosenberg |
| 5,776,092 A | 7/1998 | Farin et al. |
| 5,797,907 A | 8/1998 | Clement |
| 5,836,897 A | 11/1998 | Sakurai et al. |
| 5,836,944 A * | 11/1998 | Cosmescu ................ 606/41 |
| 5,843,109 A | 12/1998 | Mehta et al. |
| 5,868,768 A | 2/1999 | Wicherski et al. |
| 5,893,862 A | 4/1999 | Pratt et al. |
| 5,941,887 A | 8/1999 | Steen et al. |
| 5,944,737 A | 8/1999 | Tsonton et al. |
| 5,951,581 A | 9/1999 | Saadat et al. |
| 5,972,007 A | 10/1999 | Sheffield et al. |
| 6,004,318 A | 12/1999 | Garito et al. |
| 6,004,333 A | 12/1999 | Sheffield et al. |
| 6,063,050 A | 5/2000 | Manna et al. |
| 6,070,444 A | 6/2000 | Lontine et al. |
| 6,099,525 A | 8/2000 | Cosmescu |
| 6,117,134 A | 9/2000 | Cunningham et al. |
| 6,139,547 A | 10/2000 | Lontine et al. |
| 6,142,995 A | 11/2000 | Cosmescu |
| 6,146,353 A | 11/2000 | Platt, Jr. |
| 6,213,999 B1 | 4/2001 | Platt, Jr. et al. |
| 6,251,110 B1 | 6/2001 | Wampler |
| 6,257,241 B1 | 7/2001 | Wampler |
| 6,258,088 B1 | 7/2001 | Tzonev et al. |
| 6,287,344 B1 | 9/2001 | Wampler et al. |
| 6,312,441 B1 | 11/2001 | Deng |
| 6,358,281 B1 | 3/2002 | Berrang et al. |
| 6,361,532 B1 | 3/2002 | Burek |
| 6,402,748 B1 | 6/2002 | Schoenman et al. |
| 6,602,249 B1 * | 8/2003 | Stoddard et al. .......... 606/45 |
| 2004/0044342 A1 * | 3/2004 | Mackay ................ 606/45 |

FOREIGN PATENT DOCUMENTS

| | | |
|---|---|---|
| FR | 2235669 | 1/1975 |
| WO | WO 94/20032 | 9/1994 |
| WO | WO 0024329 | 5/2000 |
| WO | PCT/US01/4454 | 2/2002 |

* cited by examiner

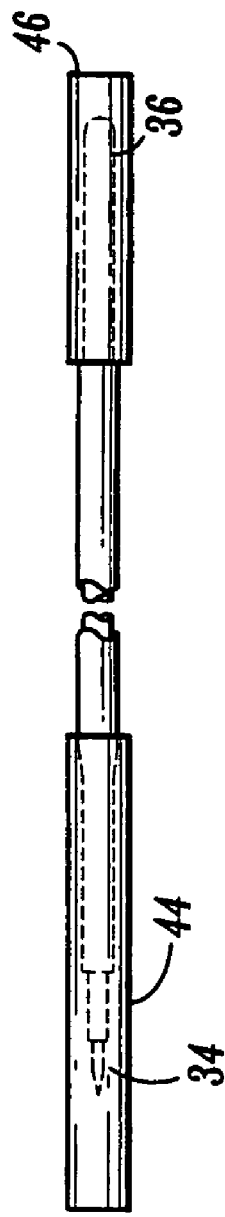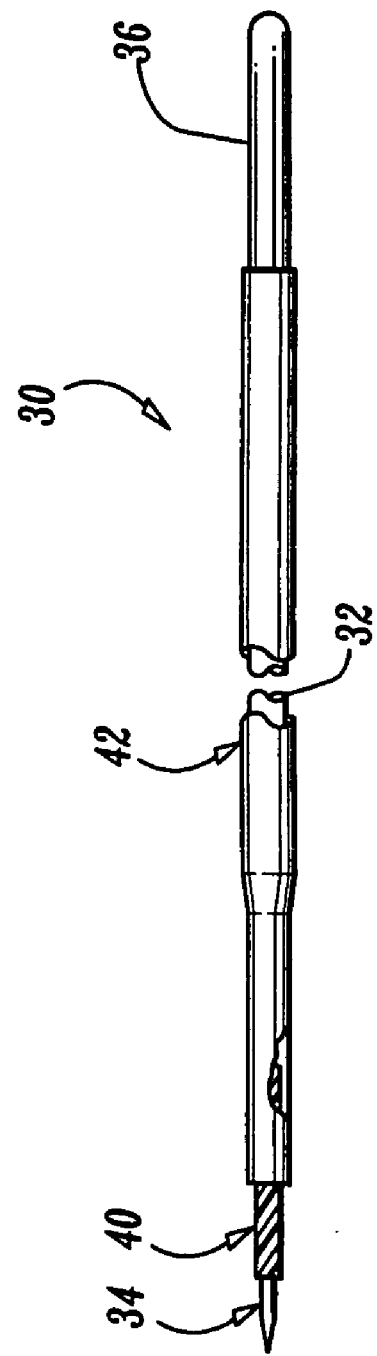

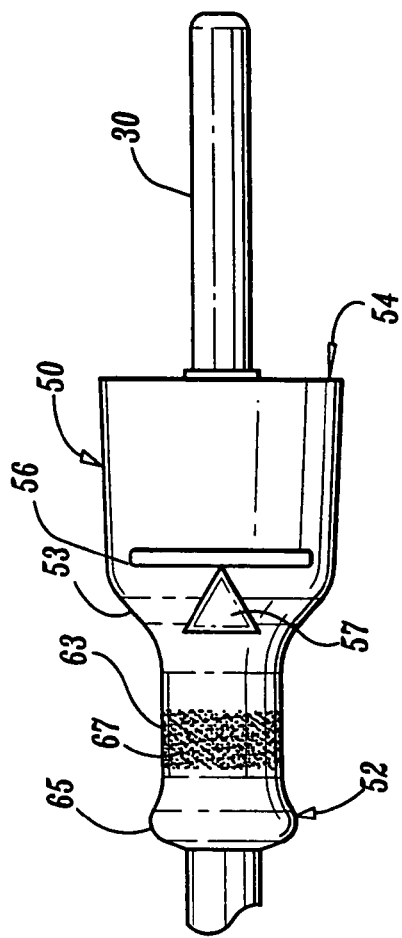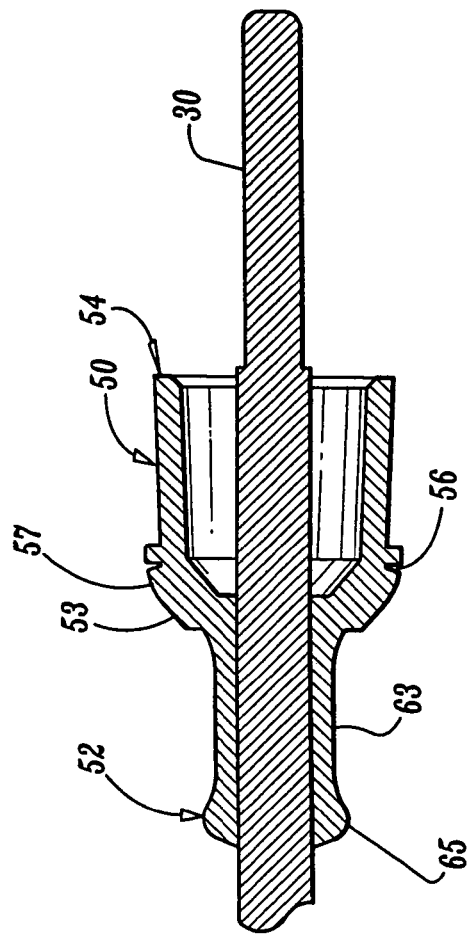

ELECTROSURGICAL ELECTRODE SHROUD

This application is a continuation of application Ser. No. 10/358,450, now U.S. Pat No. 6,986,768, filed Feb. 4, 2003.

BACKGROUND

1. Field of the Invention

The present disclosure relates to an electrode shroud and, more particularly, to an electrosurgical electrode shroud which facilitates correct insertion of the electrode into an electrosurgical instrument.

2. Description of the Related Art

As surgical knowledge and techniques have progressed, there has been a corresponding trend toward size reduction of surgical incisions and invasive instruments, thus decreasing patient trauma and contributing to rapidity of patient recovery. This has led to the practice of laparoscopic and other surgical procedures using small medical electrodes. When using medical electrodes during the performance of a surgical procedure, different types of currents can be employed for different procedures. For example, fully rectified, fully filtered currents can be used for cutting tissue; for cutting with coagulation; and for hemostasis. Spark gap currents can be used for fulguration and dessication techniques. Various electrode configurations are also available; for example, metal needles for making incisions, wire loops, round or diamond shape, for planing and contouring tissue, balls for coagulation and hemostasis, and scalpel shapes for incision and excision of tissue. In all these known electrode configurations, the working end of the electrode is electrically conductive, usually metallic, and is fully exposed, so that all sides of the electrode working end are capable of transmitting the high frequency currents to the tissue.

Thus, electrosurgical electrodes are known in the art and are used for a variety of surgical procedures. For example, U.S. Pat. No. 6,004,318 to Garito et al. discloses an electrosurgical coagulation electrode to accomplish direct cyclocoagulation for treating glaucoma. U.S. Pat. No. 4,517,975 to Garito et al. discloses an electrosurgical electrode tip adapted for a nail matrisectomy procedure.

Each of the electrosurgical electrodes discussed above and known in the prior art include a first end and a second end. The first or distal end is an active exposed tip which is used for applying the electrical signal to the patient. The active exposed tip of the first end is supported by structure that is completely electrically insulated to avoid damage to surrounding tissue, and to allow the physician to use these inactive insulated parts to help position and guide the active tip, which is the only part capable of treating tissue, during the surgical procedure.

The second or proximal end is configured for connection to an electrosurgical apparatus. More specifically, the second end is configured to be inserted into the end of an electrosurgical apparatus which provides the electrical input to the electrode. Moreover, the prior art includes provisions for assisting electrode connection to the electrosurgical apparatus. For example, the Model E2100 and Model E2550 reusable electrosurgical pencils, available from Valleylab, Boulder, Colo., include a flange on the distal end of the pencil which assists in securing the electrode to the pencil. Furthermore, the prior art includes insulated electrodes having a hard elongated opaque or solid colored boot-type shroud mounted on the end of the electrode which is configured for insertion into an electrosurgical apparatus. A function of the prior art shroud is to minimize electrical arcing between the electrode and surrounding objects at the point of connection to the electrosurgical apparatus. Examples of the prior art electrodes with opaque shrouds include model numbers E1510 through E1513 single use stainless steel electrodes which are available from Valleylab, Boulder, Colo. The prior art opaque shrouds may also include a circumferential seal formed on an inner surface of the shroud for forming a seal around the electrosurgical apparatus as it is inserted into the shroud. In another prior art technique, a section of an opaque rubber catheter having a flared end is separately fitted over the junction of the electrode and the pencil.

One advantage of the present invention over the prior art electrode shrouds is that the present invention provides the surgeon with the ability to visually confirm that the electrode is fully seated within the electrosurgical apparatus.

SUMMARY

An electrosurgical electrode shroud is provided including a hollow substantially cylindrical member having a first end portion and a second end portion; the first end portion defining an opening which is configured and dimensioned to receive an electrosurgical electrode assembly therein; and the second end portion defining an opening which is configured and dimensioned to receive an electrode mounting portion of an electrosurgical instrument, wherein at least the second end portion is formed of a substantially translucent material. The electrosurgical electrode shroud may further include a visual or tactile indicator on the second end portion for indicating a depth of penetration of the electrosurgical instrument within the second end portion when viewed by the surgeon through the translucent material.

The electrosurgical electrode shroud may further include a frustoconical transition portion between the first end portion and the second end portion. The inside diameter of the opening defined by the first end portion is preferably configured to fit an outside diameter of the electrosurgical electrode assembly received therein. The inside diameter of the opening defined by the second end portion is substantially equal to an outside diameter of the electrosurgical instrument received therein. The shroud is preferably formed of an elastomeric material to enable the shroud to be stretched to fit over the electrosurgical electrode and the electrosurgical instrument thereby ensuring a tight fit.

An electrosurgical electrode assembly is also provided having an elongate electrically-conductive shaft member with a proximal end for receiving electrosurgical currents from an electrosurgical instrument and a distal end, wherein the improvement includes an electrosurgical electrode shroud comprising a hollow substantially cylindrical member having a first end portion and a second end portion; the first end portion defining an opening which is configured and dimensioned to receive the electrosurgical electrode assembly therein; and the second end portion defining an opening which is configured and dimensioned to receive an electrode mounting portion of the electrosurgical instrument, wherein the at least second end portion is formed of a substantially translucent material. The electrosurgical electrode assembly may also include at least one layer of insulating material formed on the electrically-conductive shaft.

These features and advantages of the present disclosure will become apparent from the following detailed description of illustrative embodiments, which is to be read in connection with the accompanying drawings.

BRIEF DESCRIPTION OF THE DRAWINGS

For a better understanding of the invention, reference is made to the following description of exemplary embodiments thereof, and to the accompanying drawings, wherein:

FIG. 2 is a side view illustrating an electrosurgical electrode having a needle-shaped active tip;

FIG. 3 is a side view illustrating an electrosurgical electrode with tip protectors;

FIG. 4 is a top view illustrating an electrosurgical electrode having an electrode shroud installed thereon in accordance with the present invention;

FIG. 5 is a side cross-sectional view illustrating an electrosurgical electrode having an electrode shroud installed thereon in accordance with the present invention.

DETAILED DESCRIPTION OF PREFERRED EMBODIMENTS

The present disclosure describes an electrosurgical electrode shroud including a hollow substantially cylindrical member having a first end portion and a second end portion. The first end portion defines an opening which is configured and dimensioned to receive an electrosurgical electrode assembly therein. The second end portion defines an opening which is configured and dimensioned to receive an electrode mounting portion of an electrosurgical instrument, and at least the second end portion is formed of a substantially translucent material. As used herein, translucent is intended to encompass clear or tinted material as well as material capable of transmitting light while having sufficient diffusion to prevent perception of distinct images.

Figure 1:
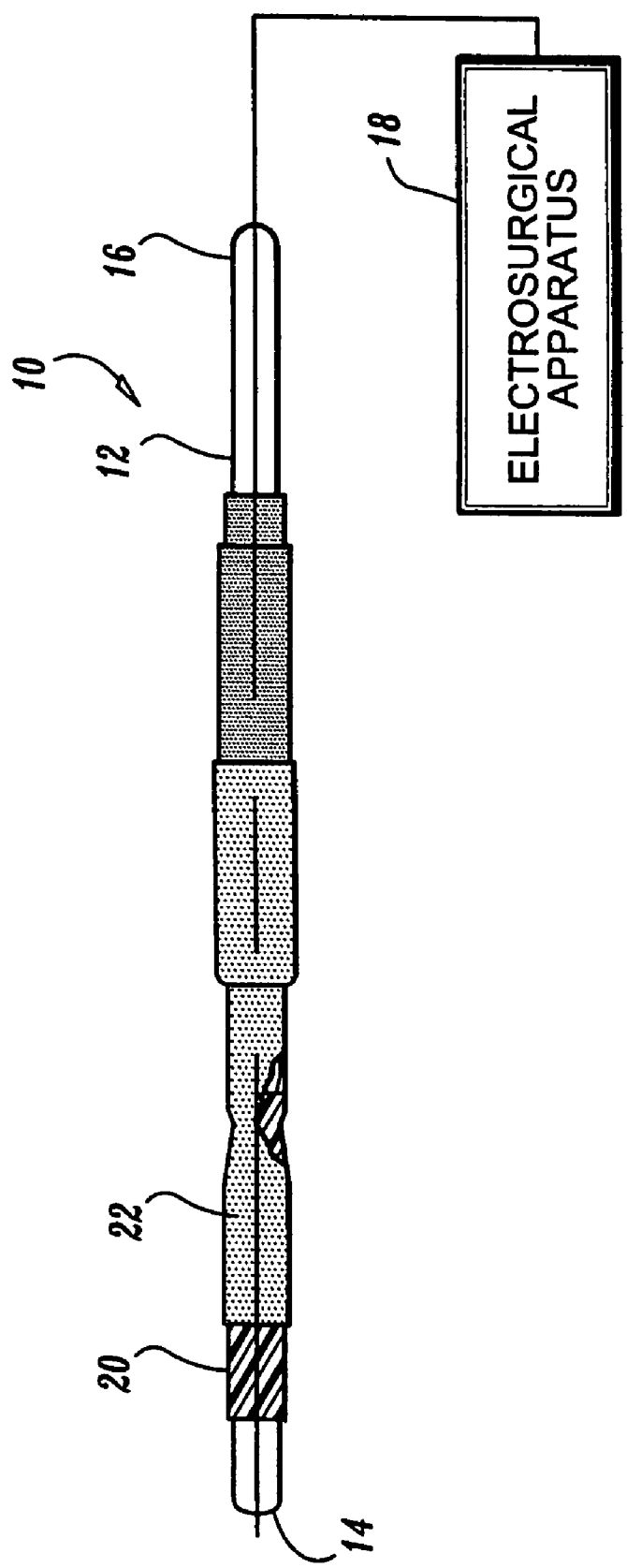
FIG. 1 is a side view illustrating an electrosurgical electrode diagrammatically connected to an electrosurgical apparatus.

Referring now in specific detail to the drawings in which like reference numerals identify similar or identical elements throughout the several views, and initially to FIG. 1, one embodiment of an electrosurgical electrode utilized in conjunction with the electrode shroud of the present disclosure is shown generally as electrosurgical electrode 10.

Electrosurgical electrode 10 includes an elongate electrically-conductive shaft member 12 with a distal end 14 and a proximal end 16. Distal end 14 is configured to receive electrosurgical currents from an electrosurgical apparatus 18. Although distal end 14 may be formed in any shape known to one having ordinary skill in the art, distal end 14 illustrated in FIG. 1 is flattened to form a thin, flat, slightly-flexible strip. The tip of distal end 14 is rounded.

The center region of electrosurgical electrode 10 is coated with first and second layers of electrically-insulating coatings 20 and 22, for example of rubber or plastic, which may be of any desired thickness. Preferably, first layer of electrically-insulating coating 20 is a PTFE coating and second layer of electrically-insulating coating 22 is a polyolefin coating. Second layer of electrically-insulating coating 22 is configured to at least partially overlap first layer of electrically-insulating coating 20. Furthermore, second layer of electrically-insulating coating 22 preferably includes a substantially conical shaped portion to prevent over insertion of the shaft member into a source of electrosurgical currents.

Referring now to FIG. 2, another embodiment of an electrosurgical electrode utilized in conjunction with the electrode shroud of the present disclosure is shown generally as electrosurgical electrode 30. Electrosurgical electrode 30 also includes an elongate electrically conductive shaft member 32 with a distal end 34 and a proximal end 36. Although distal end 34 may be formed in any shape known to one having ordinary skill in the art, distal end 34 illustrated in FIG. 2 terminates in a pointed tip similar to a needle. Distal end 34 is preferably coated with a silicon coating such as disclosed in U.S. Pat. No. 5,702,387 to Arts et al. and assigned to Valleylab Inc., Boulder, Colo.

FIG. 3 illustrates electrosurgical electrode 30 having a tip protector 44 positioned over distal end 34 and a shank protector 46 positioned over proximal end 36. Tip and shank protectors 44 and 46 protect the proximal and distal ends of electrosurgical electrode 30 during shipping and storage.

Referring now to FIGS. 4 and 5, an embodiment of an electrosurgical electrode shroud 50 in accordance with the present disclosure is illustrated. Electrosurgical electrode shroud 50 is illustrated mounted on an electrosurgical electrode 30.

Shroud 50 is formed as a hollow substantially cylindrical member having a first end portion 52 and a second end portion 54. First end portion 52 defines an opening which is configured and dimensioned to receive electrosurgical electrode assembly 30 therein. Reduced diameter section 63 and enlarged section 65 of first portion 52 facilitate gripping by the fingers of an operator during insertion and withdrawal of the electrode 30 from a pencil. Preferably gripping is enhanced by a roughened or textured surface 67 of section 63.

Second end portion 54 defines an opening which is configured and dimensioned to receive an electrode mounting portion of an electrosurgical apparatus (not shown). First end portion 52 and second end portion 54 are preferably joined by a frustoconically shaped transition portion 53. The wall thickness of second end portion 54 is preferably in the range of about 0.030 inches to about 0.050 inches. The opening in second end portion 54 is preferably molded to an angle in the range of about 5 to about 10 degrees to facilitate smoother insertion of an electrosurgical apparatus into the opening formed by second end portion 54. On a four inch electrode, a preferred length of shroud 50 is approximately 0.80 inches with first end portion 52 being approximately 0.40 inches long, transition portion 53 being approximately 0.10 inches long, and second end portion 54 being approximately 0.30 inches long.

Figure 6:
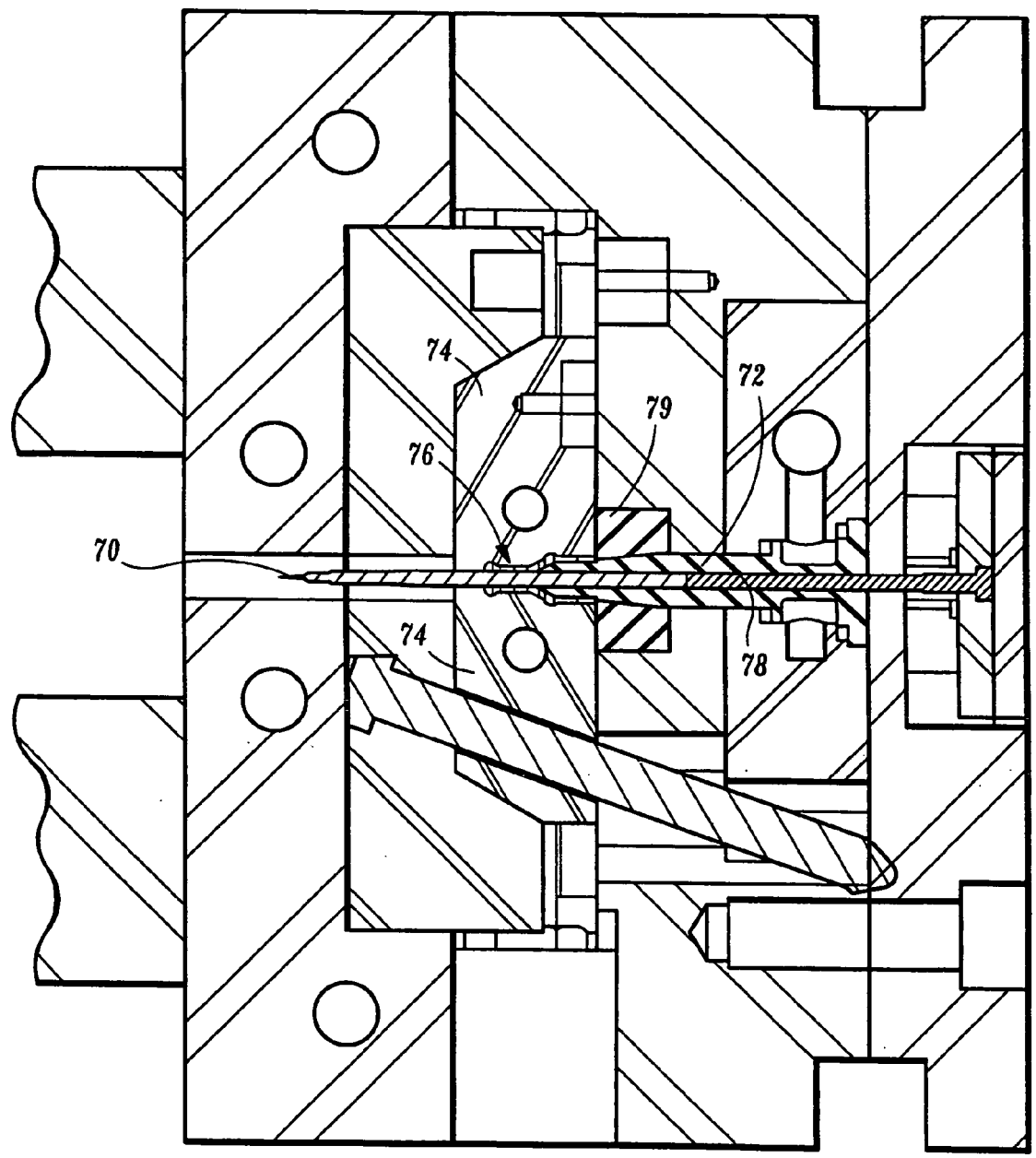
FIG. 6 is a side cross-sectional view illustrating a mold for forming a safety sleeve on an electrosurgical electrode.

To ensure a tight fit over the electrode assembly and over the electrosurgical apparatus, shroud 50 is preferably formed of an elastomeric material. In a preferred embodiment, the elastomeric material is a blue tinted thermoplastic material such as a blue 73 shore A WCPC Dynaflex resin compound available from West Coast Polymers. The resin compound is preferably formed of 49.875% GLS Dynaflex G270I TR65 Shore A, 49.875% GLS Dynaflex G2780 TR82 Shore A (each available from GLS Corporation—Thermoplastic Elastomers Division, McHenry, Ill.) and 0.25% Clariant CPE 06539 TPR Royal Blue (available from Clariant Masterbatches Division, Albion, Mich.). In a preferred embodiment, the shroud is molded over an electrode, as illustrated in FIG. 6. It is also contemplated that the shroud may be molded separately from the electrode. FIG. 6 illustrates an electrode 70 positioned within a clamshell mold 74. Electrode 70 is restrained from over-insertion into the mold by stop or alignment pin 78. A predetermined quantity of material for forming shroud 76 is forced through ports within clamshell mold 74 to form shroud 76 on electrode 70. A mandrel 72 is provided within the mold assembly to form the inner surface of one end portion of shroud 76 such that the end portion has an inner diameter which is greater than the outer diameter of electrode 70. Pin 78 and sleeve ejector 79, a stripper plate, function as a pusher to push the shroud 76 and electrode 70 out of the mold assembly once the molding process is complete.

Referring again to FIGS. 4 and 5, one purpose of the shroud 50 is to prevent over-insertion of the electrode into an electrosurgical instrument while also providing the surgeon with the ability to visually confirm that the electrode is fully seated within the electrosurgical apparatus. Thus, at least the second end portion 54 is preferably formed of a substantially translucent material which will allow the surgeon to visually confirm that the electrode is fully seated within the electrosurgical apparatus. Although second end portion 54 may be formed of a clear material, it is preferred that second end portion 54 is formed of a tinted translucent material.

Preferably, as discussed above, second end portion 54 of shroud 50 is formed of a substantially translucent material. Having at least a portion of shroud 50 formed of substantially translucent material allows the user (i.e., the surgeon, nurse, technician, etc.) to visually ascertain and confirm that electrode 70 is fully and properly coupled to and/or seated within an electrode mounting portion of an electrosurgical apparatus. As such, the uncertainty as to the connection of electrode 70 to the electrosurgical apparatus and/or the incidents of incomplete connection of electrode 70 to the electrosurgical apparatus is reduced. Accordingly, delays in performing the surgical procedure are also reduced thus, on average, tending to reduce the overall time of the surgical procedure.

The electrosurgical electrode shroud may further include a visual or tactile indicator on the second end portion for indicating a depth of penetration of the electrosurgical instrument within the second end portion. For example, second end portion 54 may include a circumferential indicator line 56 scribed thereon to provide the surgeon with a reference point against which the surgeon can gauge the depth of penetration of the electrosurgical instrument within the second end portion 54 when the electrosurgical instrument is viewed by the surgeon through the translucent material. Indicator line 56 is preferably set off by arrow 57 formed on transition portion 53. In addition, a tactile indicator may be added in the shape of a circumferential ring formed on an inner surface of second end portion 54. As the electrosurgical instrument is inserted into second end portion 54, the electrosurgical instrument will contact ring thereby providing the surgeon with an indication as to the depth of penetration.

Although the illustrative embodiments of the present invention have been described herein with reference to the accompanying drawings, it is to be understood that the invention is not limited to those precise embodiments, and that various other changes and modifications may be affected therein by one having ordinary skill in the art without departing from the scope or spirit of the invention. All such changes and modifications are intended to be included within the scope of the invention as defined by the appended claims.

What is claimed is:

1. An electrosurgical electrode shroud comprising:
a hollow substantially cylindrical member having a first end portion and a second end portion; said first end portion defining an opening which is configured and dimensioned to receive an electrosurgical electrode assembly therein; said second end portion defining an opening which is configured and dimensioned at an angle in the range of about 5 to about 10degrees to receive an electrode mounting portion of an electro surgical instrument, wherein at least said second end portion is formed of a substantially translucent material.

2. The electrosurgical electrode shroud as recited in claim 1 wherein an inside diameter of the opening defined by the first end portion is configured to fit an outside diameter of the electrosurgical electrode assembly received therein.

3. The electrosurgical electrode shroud as recited in claim 1 further comprising a transition portion between said first end portion and said second end portion.

4. The electrosurgical electrode shroud as recited in claim 3 wherein said transition portion is frustoconical in shape.

5. The electrosurgical electrode shroud as recited in claim 1 further comprising a visual indicator on said second end portion for indicating a depth of penetration of the electrosurgical instrument within said second end portion.

6. The electrosurgical electrode shroud as recited in claim 1 further comprising a tactile indicator on said second end portion for indicating a depth of penetration of the electrosurgical instrument within said second end portion.

7. The electrosurgical electrode shroud as recited in claim 1 wherein an inside diameter of the opening defined by the second end portion is substantially equal to an outside diameter of the electro surgical instrument received therein.

8. The electrosurgical electrode shroud as recited in claim 1 wherein the shroud is formed of an elastomeric material.

9. The electrosurgical electrode shroud as recited in claim 1 wherein the translucent material is substantially clear.

10. The electro surgical electrode shroud as recited in claim 1 wherein the translucent material is tinted.

11. In an electrosurgical electrode assembly having an elongate electrically-conductive shaft member with a proximal end for receiving electrosurgical currents from an electrosurgical instrument and a distal end, wherein the improvement comprises:
an electrosurgical electrode shroud comprising a hollow substantially cylindrical member having a first end portion and a second end portion; said first end portion defining an opening which is configured and dimensioned to positively receive the electrosurgical electrode assembly therein; said second end portion defining an opening which is configured and dimensioned at an angle in the range of about 5 to about 10 degrees to receive an electrode mounting portion of the electrosurgical instrument, wherein said second end portion is formed of a substantially translucent material.

12. The electro surgical electrode assembly as recited in claim 11 further comprising at least one layer of insulating material formed on said electrically-conductive shaft.

13. The electro surgical electrode assembly as recited in claim 12 further comprising a second layer of insulating material formed on said electrically-conductive shaft and at least partially covering said at least one layer of insulating material, wherein said second layer of insulating material includes a substantially conical shaped portion to prevent over insertion of the shaft member into a source of electro surgical currents.

14. The electrosurgical electrode assembly as recited in claim 11 wherein said distal end includes a needle-shaped tip portion capable of penetrating the skin of a patient and exposed electrically for applying electrosurgical currents when said shaft member is connected to a source of electrosurgical currents.

15. The electrosurgical electrode as recited in claim 11 wherein the electrode shroud is co-axial with a longitudinal axis of said shaft member.

16. The electrosurgical electrode as recited in claim 11 wherein said distal end is spade-shaped.

* * * * *